United States Patent [19]

Borcherding

[11] Patent Number: 4,983,733
[45] Date of Patent: Jan. 8, 1991

[54] PROCESS FOR PREPARING 2-AROMATIC-3-HALOBENZOTHIAZEPINES

[75] Inventor: David R. Borcherding, Roeland Park, Kans.

[73] Assignee: Marion Laboratories, Inc., Kansas City, Mo.

[21] Appl. No.: 438,303

[22] Filed: Nov. 20, 1989

[51] Int. Cl.$^5$ ............................................. C07D 281/10
[52] U.S. Cl. ..................................................... 540/491
[58] Field of Search ......................................... 540/491

[56] References Cited

U.S. PATENT DOCUMENTS 3,075,968  1/1963  Krapcho .............................. 540/491
3,895,006  7/1975  Krapcho et al. .................... 540/491
3,983,106  9/1976  Krapcho et al. .................... 540/491

OTHER PUBLICATIONS

March, "Advanced Organic Chemistry", (3rd Edition) (1985). pp. 382–384 (Wiley).

*Primary Examiner*—Robert T. Bond

[57] ABSTRACT

2-Aromatic-3-HALobenzothizepines are prepared by reaction of a 2,3-dihydro-2-aromatic-3-hydroxybenzothiazepine with a thionyl HALide. For example, dl-cis-2-(4-methoxyphenyl)-2,3-dihydro-3-hydroxy-1,5-benzothiazzepin-4(5H)-one relfuxed with thionyl chloride can prepare E-2-(4-methoxyphenyl)-3-chloro-1,5-benzothiazepin-4(5H)-one in 66 percent yield.

8 Claims, No Drawings

PROCESS FOR PREPARING 2-AROMATIC-3-HALOBENZOTHIAZEPINES

FIELD

This invention concerns preparation of 3-halobenzothiazepines, useful pharmaceuticals.

BACKGROUND

Useful 5-((substituted amino)alkyl)-2-aryl-3-halo-1,5-benzothiazepine-4(5H)-ones and 5-heterocyclicalkl-2-aryl-3-halo-1,5-benzothiazepin-4(5H)-ones are known to be prepared using as starting materials 2,3-dihydro-2-aryl1,5-benzothiazepin-(4(5H)-ones, and introducing both ethylenic unsaturation between the 2- & 3-positions and a chlorine or bromine atom into the 3-position of the benzothiazepine nucleus with N-chloro or N-bromosuccinimide. Krapcho et al., U.S. Pat. No. 3,895,006 (July 15, 1975); Krapcho et al. U.S. Pat. No. 3,983.106 (Sept. 28, 1976). See also, Krapcho, U.S. Pat. No. 3,075,967 (Jan. 29, 1963).

The art lacks and needs other routes to such and other 2-aryl-3-halobenzothiazepine compounds, and so forth.

SUMMARY

Provided is a process for preparing a 2-aromatic-3-HALObenzothiazepine comprising contacting a 2,3-dihydro-2-aromatic-3-hydroxybenzothiazepine with a thionyl HALide under conditions sufficient to prepare the 2-aromatic-3-HALObenzothiazepine.

This invention provides useful pharmaceuticals or intermediates. It is simple and efficient.

ILLUSTRATIVE DETAIL

The 2-aromatic-3-HALObenzothiazepines are benzothiazepines having an aromatic group at the 2-position of the benzothiazepine nucleus, ethylenic unsaturation between the 2- & 3-positions of the benzothiazepine nucleus, and a HALO moiety at the 3-position of the benzothiazepine nucleus, and they include any suitable salt(s) thereof. Preferably, the 2-aromatic-3-HALObenzothiazepine is a 2-aromatic-3-HALO-1,5-benzothiazepin-4(5H)-one, a compound represented by the following general formula:

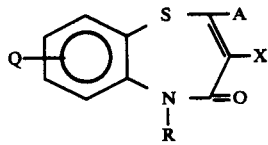
(I)

wherein
A is an aryl or substituted aryl group;
Q is a hydro (H) or halo moiety;
R is H, or a suitable organic group, and
X is a HALO moiety
or a salt thereof.

The aromatic group, to include for A, is one which is generally inert to the reaction of the process of this invention. Suitable examples of the aromatic to include aryl and substituted aryl groups include phenyl and suitably substituted phenyl such as methoxyphenyl and so forth.

The halo moiety, to include for Q, includes fluoro (F) and chloro (Cl). An H or Cl, to include 8-Cl, Q-moiety may be desired.

The suitable organic group for R includes any generally inert organic group which may reside on the heterocyclic amino group of the benzothiazepine nucleus during reaction of the process of this invention or which can be attached after formation of the ethylenic unsaturation between the 2- & 3-positions of the benzothiazepine nucleus and the HALO moiety at the 3-position of the benzothiazepine nucleus. Preferably, the suitable organic group is attached after the formation of the ethylenic unsaturation between the 2- & 3-positions of the benzothiazepine nucleus and the HALO moiety at the 3-position of the benzothiazepine nucleus. Such attachment can be by such standard N-alkylation processes as by use of a suitable organic halide, and so forth and the like, as is known in the art.

The HALO moiety, to include for X, includes bromo (Br) and Cl. Either Br or Cl may be desired.

The 2-aromatic-3-HALObenzothiazepine, to include the 2-aromatic-3-HALO-1,5-benzothiazepin-4(5H)-ones, may be a salt. Suitable salts of products alkylated to contain an alkyl amino group include acid addition salts, which can be made by processes known in the art after the formation of the ethylenic unsaturation between the 2- & 3-positions of the benzothiazepine nucleus and the HALO moiety at the 3-position of the benzothiazepine nucleus. Pharmaceutically acceptable salts may be employed.

The 2,3-dihydro-2-aromatic-3-hydroxybenzothiazepines are benzothiazepines having an aromatic group at the 2-position of the benzothiazepine nucleus, full saturation regarding, and an H-moiety at each of, the 2- & 3-positions of the benzothiazepine nucleus, and a hydroxy (OH) moiety at the 3-position of the benzothiazepine nucleus. These can be obtained or prepared by known processes or by processes analogous thereto. Preferably, the 2,3-dihydro-2-aromatic-3-hydroxybenzothiazepine is a cis-2,3-dihydro-2-aromatic-3-hydroxy-1,5-benzothiazepin-4(5H)-one, a compound represented by the following general formula:

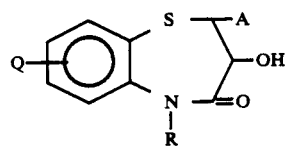
(II)

wherein A, Q & R are as defined above and for the formula I. These, too, can be obtained or prepared by known processes or by processes analogous thereto. See e.g., patents classified in U.S. Pat. class 540 subclass 491.

The thionyl HALide is a compound represented by the following general formula:

$$SOX_2 \qquad (III)$$

wherein X is independently at each occurrence HALO as above. Preferably, both HALO moieties of the thionyl HALide are the same. Suitable examples include thionyl bromide and thionyl chloride. The thionyl HALides can be obtained or prepared by known processes or by processes analogous thereto.

In the practice of this invention, the 2,3-dihydro-2-aromatic-3-hydroxybenzothiazepine is contacted with the thionyl HALide. In general, conditions are those sufficient to prepare the 2-aromatic-3-HALObenzothiazepine.

The 2,3-dihydro-2-aromatic-3-hydroxybenzothiazepine and the thionyl HALide can be contacted neat. Alternatively, they may be contacted in the presence of a suitable diluent. In any event, a mixture generally results.

Amounts of the 2,3-dihydro-2-aromatic-3-hydroxybenzothiazepine and the thionyl HALide can vary. Typically, the thionyl HALide is used in molar excess. Nonetheless, molar ratios of the 2,3-dihydro-2-aromatic-3-hydroxybenzothiazepine to the thionyl HALide may be about from 1:2 to 1:20.

The mixture is advantageously heated. The heating may be carried out under reflux conditions.

Times of the contact to include any heating can vary. Times may be about from half an hour to a score (20) hours.

An inert atmosphere may be employed. Suitable inert atmospheres include argon, helium and nitrogen gases.

Product 2-aromatic-3-HALObenzothiazepine may be isolated and recovered by known methods. Preferably, the product is a solid and suitable isolation and recovery methods are employed with this in mind.

Yields of the product can be excellent. Preferably, the yields are at least about 50 or at least about 60 percent of theory.

The following further illustrates this invention.

EXAMPLE

Under a nitrogen blanket, a 2.0 g sample of dl-cis-2-(4-methoxyphenyl)-2,3-dihydro-3-hydroxy-1,5-benzothiazepin-4(5H)-one (6.8 mmol) was refluxed neat with 20 mL of thionyl chloride (27.6 mmol) for approximately 2 hours. Then, 50 mL of hexane and about 20 mL of ether were added, and solid product was filtered off. The solid was dried under vacuum to obtain 1.4 g of 2-(4-methoxyphenyl)-3-chloro-1,5-benzothiazepin-4(5H)-one (66 percent yield of theory).

CONCLUSION

The present invention is thus provided. Numerous adaptations and modifications can be effected by those skilled in the art within the spirit of this invention, the scope of which is particularly pointed out by the following distinctly claimed subject matter.

What is claimed is:

1. A process for preparing a 2-aromatic-3HALObenzothiazepine comprising contacting a 2,3-dihydro-2-aromatic-3-hydroxybenzothiazepine with a thionyl HALide under conditions sufficient to prepare the 2-aromatic-3-HALObenzothiazepine.

2. The process of claim 1, wherein the 2-aromatic-3-HALObenzothiazepine is a 2-aromatic-3-HALO-1,5-benzothiazepin-4(5H)-one, a compound represented by the following general formula:

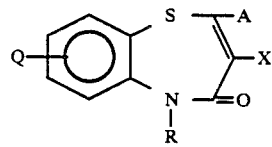

wherein
A is an aryl or substituted aryl group;
Q is a hydro (H) or halo moiety;
R is H, or a suitable organic group, and
X is a HALO moiety,
or a salt thereof; the 2,3-dihydro-2-aromatic-3-hydroxybenzothiazepine is a cis-2,3-dihydro-2-aromatic-3-hydroxy-1,5-benzothiazepin-4(5H)-one, a compound represented by the following general formula:

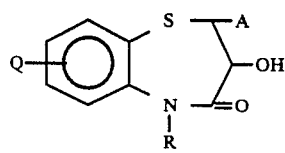

wherein A, Q & R are as defined above and for the formula I, and the thionyl HALide is a compound represented by the following general formula:

$$SOX_2 \qquad (III)$$

wherein X is independently at each occurrence HALO as above.

3. The process of claim 2, wherein
A is phenyl or substituted phenyl;
Q is H or Cl;
R is H;
X is Br, and
the contact is carried out substantially neat.

4. The process of claim 2, wherein
A is phenyl or substituted phenyl;
Q is H or Cl;
R is H;
X is Cl, and
the contact is carried out substantially neat.

5. The process of claim 1, 2, 3 or 4, which yields the 2-aromatic-3-HALObenzothiazepine at lease about 50 percent of theory.

6. The process of claim 5, which yields the 2-aromatic-3-HALObenzothiazepine at the least about 60 percent of theory.

7. A process for preparing 2-(4-methoxyphenyl)-3-chloro-1,5-benzothiazepin-4(5H)-one comprising contacting dl-cis-2-(4-methoxyphenyl)-2,3-dihydro-3-hydroxy-1,5-benzothiazepin-4(5H)-one and thionyl chloride to form a mixture, refluxing the mixture, and recovering the 2-(4-methoxyphenyl)-3-chloro-1,5-benzothiazepin-4 (5H)-one at a yield of at least about 60 percent of theory.

8. The process of claim 7, which yields the 2-(4-methoxyphenyl)-3-chloro-1,5-benzothiazepin-4(5H)-one at at least about 66 percent of theory.

* * * * *

UNITED STATES PATENT AND TRADEMARK OFFICE
CERTIFICATE OF CORRECTION

PATENT NO. : 4,983,733
DATED : January 8, 1991
INVENTOR(S) : David R. Borcherding It is certified that error appears in the above-identified patent and that said Letters Patent is hereby corrected as shown below:

On the Title Page, at line 1, of the Abstract, the patent reads "HALobenzothizepines", should read --HALObenzothiazepines-- On the Title Page at lines 4-5 of the Abstract, the patent reads "5-benzothiazzepin" should read --5-benzothiazepin--. At column 1, line 11, the patent reads "5-heterocyclicalkl-" and should read -- 5-heterocyclicalkyl- --. At column 1, line 15, the patent reads "aryl1,5" and should read --aryl-1,5--. At column 1, line 61, the patent reads "moiety" and should read --moiety,--. At column 4, claim 2, line 30, the patent reads "SOX21" and should read --SOX2--

Signed and Sealed this

Twenty-second Day of December, 1992

Attest:

DOUGLAS B. COMER

*Attesting Officer*  *Acting Commissioner of Patents and Trademarks*